(12) United States Patent
Karrowni

(10) Patent No.: US 10,737,069 B2
(45) Date of Patent: Aug. 11, 2020

(54) RETRO ACCESS VASCULAR SHEATH AND RELATED METHODS

(71) Applicant: Kar Health, LLC, Des Moines, IA (US)

(72) Inventor: Wassef Karrowni, Irvine, CA (US)

(73) Assignee: Kar Health, LLC, Des Moines, IA (US)

( * ) Notice: Subject to any disclaimer, the term of this patent is extended or adjusted under 35 U.S.C. 154(b) by 28 days.

(21) Appl. No.: 16/127,414

(22) Filed: Sep. 11, 2018

(65) Prior Publication Data

US 2019/0076627 A1 Mar. 14, 2019

Related U.S. Application Data

(60) Provisional application No. 62/557,221, filed on Sep. 12, 2017.

(51) Int. Cl.
| | |
|---|---|
| *A61M 25/06* | (2006.01) |
| *A61M 25/09* | (2006.01) |
| *A61M 25/00* | (2006.01) |
| *A61M 25/01* | (2006.01) |

(52) U.S. Cl.
CPC .... *A61M 25/0662* (2013.01); *A61M 25/0054* (2013.01); *A61M 25/0905* (2013.01); *A61M 25/0138* (2013.01); *A61M 25/09041* (2013.01); *A61M 2025/0024* (2013.01); *A61M 2025/0175* (2013.01); *A61M 2025/0675* (2013.01)

(58) Field of Classification Search
CPC .......... A61M 25/0062; A61M 25/0054; A61M 25/0905; A61M 25/0138; A61M 25/09041; A61M 25/0021; A61M 25/0041; A61M 25/023; A61M 2025/0024; A61M 2025/0127; A61M 2025/0675; A61M 2025/0175; A61M 2205/6045; A61B 17/3421; A61B 2034/107; A61B 2017/00331; A61B 2017/00991; A61B 2017/003

See application file for complete search history.

(56) References Cited

U.S. PATENT DOCUMENTS

| | | | | |
|---|---|---|---|---|
| 5,891,057 | A * | 4/1999 | Chaisson | A61M 25/0041 600/435 |
| 6,030,414 | A * | 2/2000 | Taheri | A61F 2/07 623/1.1 |
| 6,273,881 | B1 * | 8/2001 | Kiemeneij | A61M 25/0041 604/532 |
| 8,998,936 | B2 * | 4/2015 | Alvarez | A61M 25/0194 606/159 |
| 2009/0192494 | A1 * | 7/2009 | Michishita | A61M 25/0041 604/525 |
| 2010/0262087 | A1 * | 10/2010 | Coppi | A61M 25/0662 604/246 |
| 2014/0221898 | A1 * | 8/2014 | Kurrus | A61M 25/003 604/6.16 |
| 2018/0338846 | A1 * | 11/2018 | Folan | A61B 17/3423 |

* cited by examiner

*Primary Examiner* — Anh T Dang
(74) *Attorney, Agent, or Firm* — Davis, Brown, Koehn, Shors & Roberts, P.C.; Sean D. Solberg

(57) ABSTRACT

Disclosed herein are various vascular sheath embodiments for use in the introduction of interventional devices into a blood vessel of a patient. More specifically, disclosed herein are embodiments of a vascular sheath having at least one side access opening and at least one flexible area substantially adjacent to the side access opening.

7 Claims, 3 Drawing Sheets

RETRO ACCESS VASCULAR SHEATH AND RELATED METHODS

CROSS-REFERENCE TO RELATED APPLICATION(S)

This application claims the benefit under 35 U.S.C. § 119(e) to U.S. Provisional Application 62/557,221, filed Sep. 12, 2017 and entitled "Retro Access Vascular Sheath and Related Methods," which is hereby incorporated herein by reference in its entirety.

FIELD OF THE INVENTION

The various embodiments herein relate to vascular sheaths for use in cardio interventional procedures and methods for using same.

BACKGROUND OF THE INVENTION

In vascular interventions, an introducer sheath is used to deliver wires and interventional devices as needed to complete a cardio interventional procedure. The sheath is typically inserted into the target vessel using a known Seldinger technique such that the sheath is inserted in a specific direction (either upstream or downstream in the vessel) that depends on the vascular bed being targeted. For example, if the target area is upstream from the point of insertion, then the sheath is disposed such that the distal end is directed upstream within the vessel. In contrast, if the target area is downstream from the point of insertion, then the sheath is disposed such that the distal end is directed downstream within the vessel.

However, in certain procedural situations, including peripheral arterial interventions, for example, it is sometimes desirable to re-direct the position of a sheath within a vessel by 180 degrees after it has already been inserted into the vessel and positioned in one direction in order to access a different vascular target area. However, known technologies don't currently provide for such re-direction of a sheath in the same procedure, because the risks can include (1) loss of the access site, (2) damage to the vessel wall, and/or (3) significant bleeding from the access site, leading to hematomas. Instead, in the current state of the art, if a different vascular target area becomes desirable after the sheath has already been inserted in the other direction within a target vessel, it is necessary to create another puncture in another vessel. In fact, it is typically not safe to make a second puncture in a second vessel on the same day, so not only does the known procedure require a second puncture, but it can also require a second procedure on a second day.

There is a need in the art for improved vascular sheaths and methods for using the same.

BRIEF SUMMARY OF THE INVENTION

Discussed herein are various vascular sheath embodiments and related methods, each having at least one side access opening and at least one flexible area along the length of the sheath. The various embodiments relate to sheaths and methods that allow interventional devices to access either direction in a blood vessel without having to remove the sheath.

In Example 1, a vascular sheath comprises an elongate body, a lumen defined within the body, a distal opening defined at a distal end of the body, wherein the distal opening is in fluidic communication with the lumen, a proximal opening defined at a proximal end of the body, wherein the proximal opening is in fluidic communication with the lumen, at least one side access opening defined in the body, wherein the at least one side access opening is positioned between the distal opening and the proximal opening, and at least one flexible area disposed substantially adjacent to the side access opening.

Example 2 relates to the vascular sheath according to Example 1, wherein the at least one flexible area is disposed along a length of the elongate body.

Example 3 relates to the vascular sheath according to Example 1, wherein the at least one flexible area is disposed axially adjacent to the side access opening.

Example 4 relates to the vascular sheath according to Example 1, wherein the at least one flexible area comprises a first flexible area axially adjacent to the at least one side access opening on a first side of the at least one side access opening, and a second flexible area axially adjacent to the at least one side access opening on a second side of the at least one side access opening.

Example 5 relates to the vascular sheath according to Example 1, wherein the at least one side access opening comprises a first side access opening defined in the body, and a second side access opening defined in the body, wherein the second side access opening is radially adjacent to the first side access opening.

Example 6 relates to the vascular sheath according to Example 1, wherein the at least one side access opening comprises a first side access opening defined in the body, and a second side access opening defined in the body, wherein the second side access opening is disposed on a radially opposite side of the body in relation to the first side access opening.

Example 7 relates to the vascular sheath according to Example 1, wherein the elongate body comprises a distal portion extending from the distal opening to the at least one side access opening, and a proximal portion extending from the proximal opening to the at least one side access opening, wherein the at least one flexible area is configured to allow the proximal portion to be movable in relation to the distal portion at the at least one flexible area such that the proximal portion can be disposed at an angle in relation to the distal portion that is greater than 90 degrees.

In Example 8, a vascular sheath comprises an elongate body, a lumen defined within the body, a distal opening defined at a distal end of the body, wherein the distal opening is in fluidic communication with the lumen, a proximal opening defined at a proximal end of the body, wherein the proximal opening is in fluidic communication with the lumen, at least one flexible joint disposed on the elongate body between the distal opening and the proximal opening, and at least one side access opening defined in the at least one flexible joint.

Example 9 relates to the vascular sheath according to Example 8, wherein the at least one flexible joint is a concertina-type joint.

Example 10 relates to the vascular sheath according to Example 8, wherein the at least one flexible joint comprises a first flexible area axially adjacent to the at least one side access opening on a first side of the at least one side access opening, and a second flexible area axially adjacent to the at least one side access opening on a second side of the at least one side access opening.

Example 11 relates to the vascular sheath according to Example 8, wherein the at least one side access opening comprises a first side access opening defined in the body, and a second side access opening defined in the body, wherein the second side access opening is radially adjacent to the first side access opening.

Example 12 relates to the vascular sheath according to Example 11, wherein the at least one flexible joint comprises a first flexible area axially adjacent to the first and second side access openings on a first axial side of the first and second side access openings, and a second flexible area axially adjacent to the first and second side access openings on a second, opposite axial side of the first and second side access openings.

Example 13 relates to the vascular sheath according to Example 8, wherein the at least one side access opening comprises a first side access opening defined in the body, and a second side access opening defined in the body, wherein the second side access opening is disposed on a radially opposite side of the body in relation to the first side access opening.

Example 14 relates to the vascular sheath according to Example 8, wherein the elongate body comprises a distal portion extending from the distal opening to the at least one flexible joint, and a proximal portion extending from the proximal opening to the at least one flexible joint, wherein the at least one flexible joint is configured to allow the proximal portion to be movable in relation to the distal portion at the at least one flexible joint such that the proximal portion can be disposed at an angle in relation to the distal portion that is greater than 90 degrees.

In Example 15, a method of performing an interventional cardiac procedure comprises inserting a distal end of an elongate body of a vascular sheath through an incision and into a blood vessel, positioning the distal end of the vascular sheath in a first direction in relation to blood flow in the blood vessel, advancing a distal portion of an interventional device distally through a proximal opening in the vascular sheath, through a lumen defined within the vascular sheath, out of a distal opening in the vascular sheath and toward a first target area in the blood vessel, retracting the distal portion of the interventional device proximally through the distal opening and past an at least one side access opening defined in the elongate body, bending the elongate body at a flexible area disposed along the elongate body such that the proximal end of the vascular sheath is urged closer to the distal end, advancing the distal portion of the interventional device distally out of the at least one side access opening in a second direction in relation to the blood flow in the blood vessel toward a second target area in the blood vessel, and retracting the distal portion of the interventional device proximally through the at least one side access opening and through the proximal opening of the vascular sheath and out of the lumen.

Example 16 relates to the method according to Example 15, further comprising retracting the distal end of the elongate body of the vascular sheath from the blood vessel after retracting the distal portion of the interventional device out of the lumen.

Example 17 relates to the method according to Example 15, further comprising retracting the elongate body of the vascular sheath until the flexible area of the elongate body is disposed within the incision prior to bending the elongate body.

Example 18 relates to the method according to Example 15, further comprising positioning the at least one side access opening adjacent to the incision prior to bending the elongate body.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

The various embodiments herein relate to a retro or dual-direction vascular sheath that can be inserted into a blood vessel in one direction and then adjusted to allow for access in the other direction without having to remove the sheath, and related methods.

Figure 1:
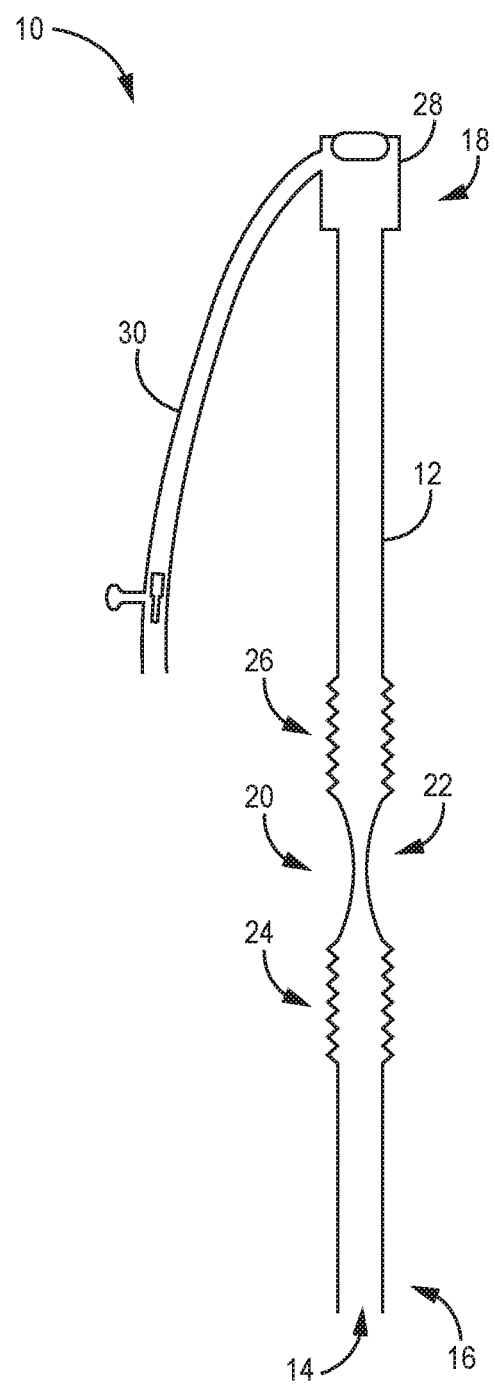
FIG. 1 is a side view of a vascular sheath, according to one embodiment.

One exemplary embodiment of a sheath 10 is provided in FIG. 1. The sheath 10 has a body 12 with a lumen 14 defined therethrough. The sheath 10 has a distal end 16 and a proximal end 18, wherein the proximal end includes a known three-way stop cock 28 and a side tube 30. Alternatively, the sheath 10 can have any known sheath components at or near the proximal end 18. The sheath 10 accommodates a dilator (not shown) that can be inserted into the lumen 14 through the stop cock 28 at the proximal end 18 and extends distally out of the distal end 16. In addition, the sheath 10 has first and second mid-length openings 20, 22 defined within the body 12 of the sheath 10, both of which also provide fluidic access to the lumen 14. In this embodiment, the two openings 20, 22 are disposed on opposite sides of the body 12 and radially adjacent as depicted. In accordance to one embodiment as shown, each of the openings 20, 22 has a curved or crescent shape as shown in the figure. Alternatively, the openings 20, 22 can have any other known shape for an opening in a sheath. Further, the sheath can have two flexible areas or joints 24, 26 along the length of the body 12. According to one embodiment, the flexible areas 24, 26 allow the sheath body 12 to bend at an angle exceeding 90 degrees. In this specific example, the flexible areas 24, 26 are positioned distally and proximally of the openings 20, 22 as shown. It is understood that these two flexible areas can also be described as a single flexible area 24, 26 with the two openings 20, 22 defined within the flexible area 24, 26. Alternatively, the flexible areas 24, 26 can be positioned anywhere along the length of the sheath body 12.

In one implementation, the flexible areas 24, 26 in the sheath body 12 are a series of grooves or ribs 24, 26 formed in the body 12, thereby creating flexibility in the body 12 where the grooves or ribs 24, 26 are located on the body 12. That is, in certain embodiments, the flexible areas 24, 26 form joints or hinges 24, 26 that are concertina-type joints or hinges 24, 26. Alternatively, the flexible areas 24, 26 can be created mechanically via any feature or component that is known to create flexibility in a sheath, catheter, or similar medical device. It is understood that any of the flexible areas in any implementations disclosed or contemplated herein can have features or structures similar or identical to those described above with respect to the flexible areas 24, 26.

Figure 3:
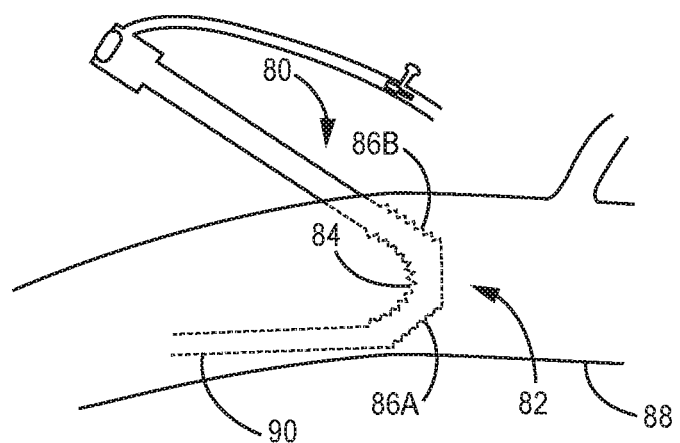
FIG. 3 is a cross-sectional side view of another vascular sheath positioned in a blood vessel, according to a further embodiment.

According to one alternative, instead of two mid-length openings 20, 22 as shown in FIG. 1, the sheath can have only one opening on one side of the sheath body. For example, a sheath 80 having one mid-length opening 82 is shown in FIG. 3, according to one embodiment. In this embodiment, the sheath 80 also has one flexible area 84 on one side (without the opening) and two flexible areas 86A, 86B on the other side: a distal flexible area 86A and a proximal flexible area 86B. According to one implementation, the single mid-length opening 82 is formed in the side of the sheath 80 from which the side tube (not shown) extends, while in another implementation, the opening 82 is formed on the side opposite the side from which the side tube extends.

Figure 2A:
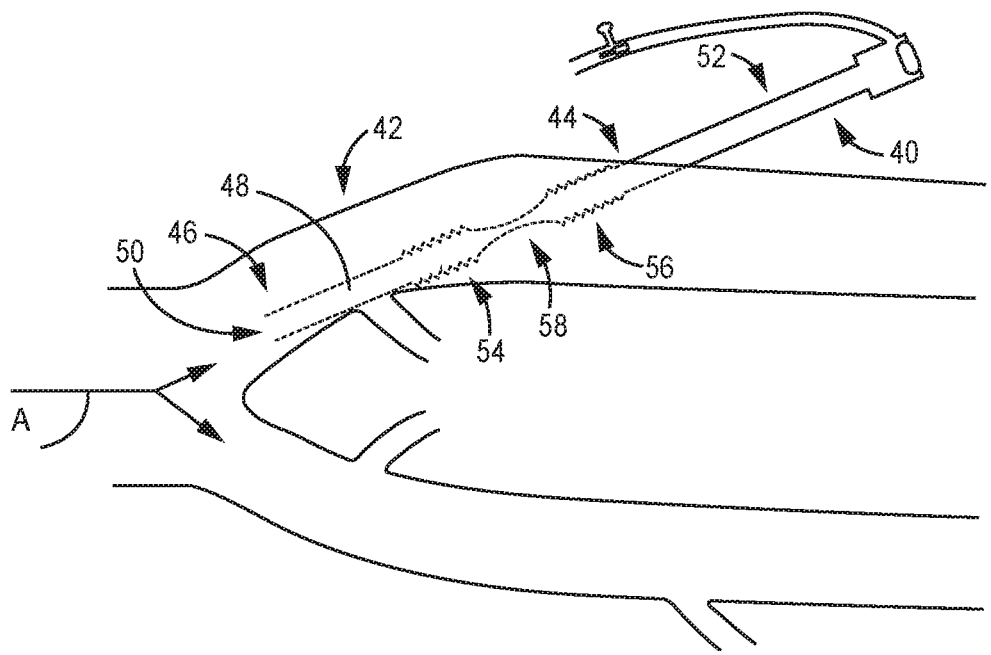
FIG. 2A is a cross-sectional side view of a vascular sheath being positioned in a blood vessel, according to one embodiment.

In use, the embodiments disclosed or contemplated herein can be used to insert a sheath into a blood vessel in one direction and then provide access to the other direction as necessary. For example, in one embodiment as depicted in FIG. 2A, a sheath 40 is inserted into a blood vessel 42 through an incision 44. In this implementation, the distal end 46 of the sheath 40 is inserted upstream (antegrade) in relation to the blood flow, which is depicted by arrow A, as shown. In this position, any interventional medical device can be introduced through the lumen 48 of the sheath 40 and out of the opening 50 at the distal end of the sheath 40 and advanced toward the target area.

Figure 2B:
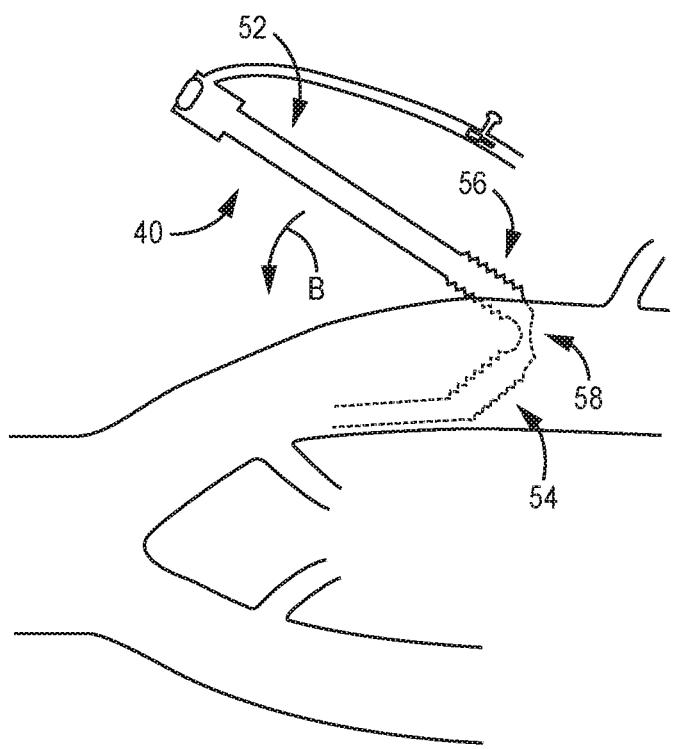
FIG. 2B is a cross-sectional side view of the vascular sheath of FIG. 2A being retracted and bent to allow access for the interventional device in the opposite direction in the blood vessel, according to one embodiment.

However, if it is determined that an interventional device must be inserted downstream/in the retrograde direction (in the opposite direction of the distal end 46 of the sheath 40), a user (such as, for example, a surgeon) can take the following steps. First, as best shown in FIG. 2B, the user can urge the proximal end 52 of the sheath 40 forward (toward the distal end 46 of the sheath 40 in the direction depicted by arrow B) so that sheath 40 bends at the flexible areas 54, 56 such that the proximal end 52 is closer to the distal end 46 of the sheath 40. Once this bent configuration is achieved as depicted in FIG. 2B, the next step is that a device can be inserted through the sheath 40 such that the device extends out of the mid-length opening 58 in the direction opposite of the distal end 46, which, in this specific example, is downstream. That is, the bending of the sheath 40 and the insertion of the interventional device through the sheath 40 and out of the opening 58 allow for device access in the direction opposite the originally desired direction.

Once the procedure is completed, the interventional device can be retracted such that the device retracts through the mid-length opening 58, through the proximal portion of the sheath 40 and out of the sheath 40. At this point, the sheath 40 can be urged back into its original configuration as best shown in FIG. 2A and itself removed from the blood vessel 42 through the incision 44.

According another implementation, the alternative sheath 80 discussed above and depicted in FIG. 3 can be used in a similar fashion to the sheath 40. However, when using the alternative sheath 80, in one exemplary embodiment, the user positions the sheath 80 so that the mid-length opening 82 is accessible to the direction of the blood vessel 88 that is opposite the direction that the distal end 90 of the sheath 80 is disposed.

Although the present invention has been described with reference to preferred embodiments, persons skilled in the art will recognize that changes may be made in form and detail without departing from the spirit and scope of the invention.

What is claimed is:

1. A method of performing an interventional cardiac procedure, the method comprising:
   inserting a distal end of an elongate body of a vascular sheath through an incision and into a blood vessel;
   positioning the distal end of the vascular sheath in a first direction in relation to blood flow in the blood vessel;
   advancing a distal portion of an interventional device distally through a proximal opening in the vascular sheath, through a lumen defined within the vascular sheath, out of a distal opening in the vascular sheath and toward a first target area in the blood vessel;
   retracting the distal portion of the interventional device proximally through the distal opening and past an at least one side access opening defined in the elongate body;
   bending the elongate body at a flexible area disposed along the elongate body such that the proximal end of the vascular sheath is urged closer to the distal end;
   advancing the distal portion of the interventional device distally out of the at least one side access opening in a second direction in relation to the blood flow in the blood vessel toward a second target area in the blood vessel; and
   retracting the distal portion of the interventional device proximally through the at least one side access opening and through the proximal opening of the vascular sheath and out of the lumen.

2. The method of claim 1, further comprising retracting the distal end of the elongate body of the vascular sheath from the blood vessel after retracting the distal portion of the interventional device out of the lumen.

3. The method of claim 1, further comprising retracting the elongate body of the vascular sheath until the flexible area of the elongate body is disposed within the incision prior to bending the elongate body.

4. The method of claim 1, further comprising positioning the at least one side access opening adjacent to the incision prior to bending the elongate body.

5. The method of claim 1, wherein the first direction is upstream in relation to blood flow.

6. The method of claim 1, wherein the at least one side access opening comprises two side access openings.

7. The method of claim 6, wherein the two side access openings are radially adjacent to each other.

* * * * *